US007288067B2

(12) United States Patent
Ahmed

(10) Patent No.: US 7,288,067 B2
(45) Date of Patent: *Oct. 30, 2007

(54) TONOMETER AND METHOD OF USE

(76) Inventor: A. Mateen Ahmed, 10763 Edison Ct., Rancho Cucamonga, CA (US) 91730

( * ) Notice: Subject to any disclaimer, the term of this patent is extended or adjusted under 35 U.S.C. 154(b) by 158 days.

This patent is subject to a terminal disclaimer.

(21) Appl. No.: 11/185,932

(22) Filed: Jul. 20, 2005

(65) Prior Publication Data

US 2006/0020194 A1   Jan. 26, 2006

Related U.S. Application Data

(63) Continuation of application No. 10/300,089, filed on Nov. 20, 2002, now Pat. No. 6,923,765.

(60) Provisional application No. 60/332,198, filed on Nov. 21, 2001.

(51) Int. Cl.
*A61B 3/16* (2006.01)

(52) U.S. Cl. .................................................. 600/399
(58) Field of Classification Search ................ 600/398, 600/399, 401, 403, 405, 561, 587; 73/79
See application file for complete search history.

(56) References Cited

U.S. PATENT DOCUMENTS 6,923,765 B2 *   8/2005   Ahmed ......................... 600/399

* cited by examiner

*Primary Examiner*—Max Hindenburg
*Assistant Examiner*—Brian Szmal
(74) *Attorney, Agent, or Firm*—John J. Connors; Connors & Assoc. Inc.

(57) ABSTRACT

A device used to measure intraocular pressure within a patient's eye includes a probe typically having an end to which is attached a resilient member with a hollow interior that decreases in volume as the member is pressed against the eye. The greater the intraocular pressure within an eye, the more the volume decreases. A liquid moves in response to this change and this movement is detected to signal if the intraocular pressure is at a safe level.

11 Claims, 5 Drawing Sheets

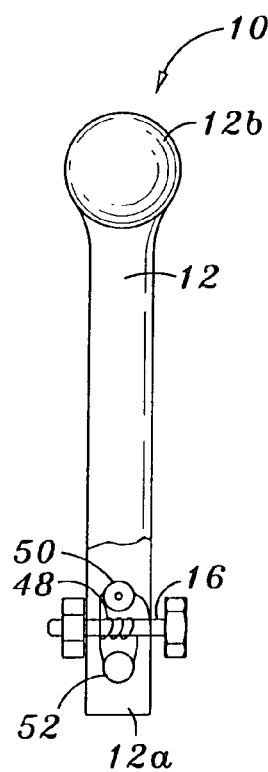
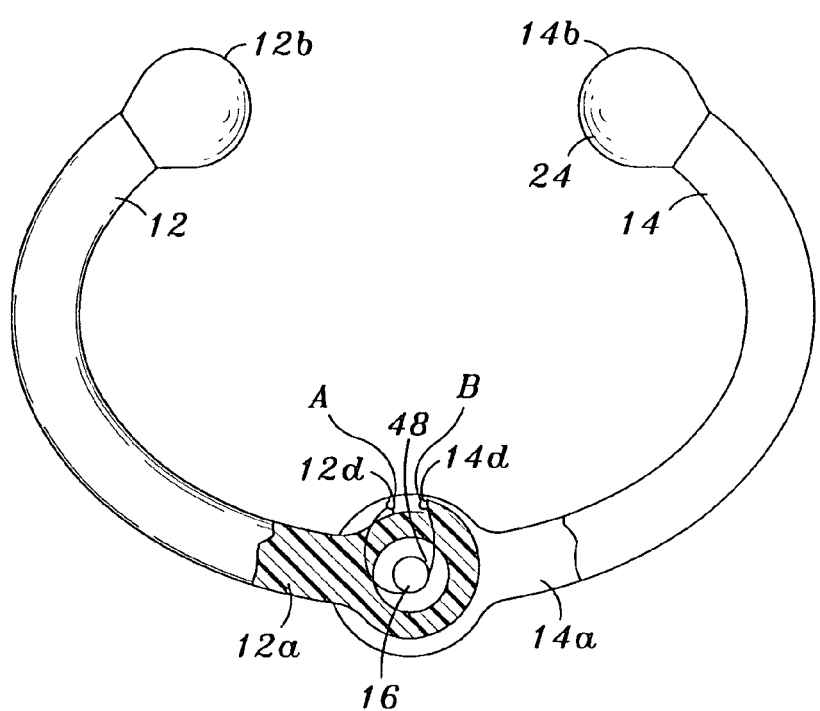
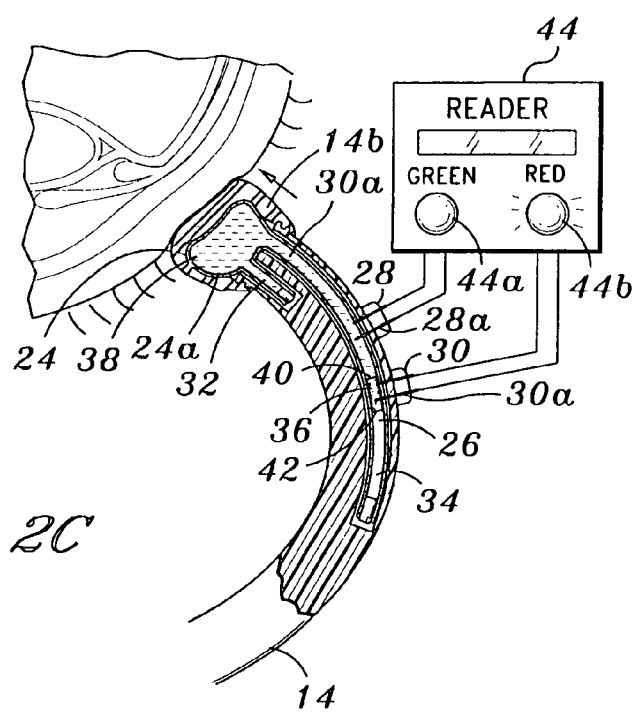
Fig. 2A  Fig. 2B
Fig. 2C

TONOMETER AND METHOD OF USE

RELATED PATENT APPLICATIONS & INCORPORATION BY REFERENCE

This application is a continuation application of utility application Ser. No. 10/300,089, filed Nov. 20, 2002, now U.S. Pat. No. 6,923,765 B2, which claims the benefit under 35 USC 119 (e) of U.S. provisional patent application Ser. No. 60/332,198, entitled "Tonometer & method Of Use," filed Nov. 21, 2001. These related application are incorporated herein by reference and made a part of this application. If any conflict arises between the disclosure of the invention in these utility applications and that in the related provisional application, the disclosure in these utility applications shall govern. Moreover, Applicant incorporates herein by reference any and all U.S. patents, U.S. patent applications, and other documents cited or referred to in this application or cited or referred to in the U.S. patents and U.S. patent applications incorporated herein by reference.

DEFINITIONS

The words "comprising," "having," and "including," and other forms thereof, are intended to be equivalent in meaning and be open ended in that an item or items following any one of these words is not meant to be an exhaustive listing of such item or items, or meant to be limited to only the listed item or items.

BACKGROUND OF THE INVENTION

Tonometers are well-known devices for detecting the intraocular pressure within an eye. There are several types of tonometers available. In general, the commercially available tonometers require that the eyelid be open and the device contact directly or indirectly the open eye. For example, one type of tonometer uses a jet of gas that impinges against the open eye. Another type has a probe that makes physical contact with the open eye. Such conventional tonometers are expensive, and not particularly accurate. Moreover, their use frequently irritates to the patient's eye. Consequently, it would be desirable to provide a tonometer that could detect the intraocular pressure through the closed eyelid of a patient. Furthermore, it would be desirable to provide an inexpensive device which patients could use themselves.

SUMMARY OF INVENTION

This invention, with its several desirable features, is summarized in the CLAIMS that follow. After reading the following section entitled "DETAILED DESCRIPTION OF SOME EMBODIMENTS OF THIS INVENTION," one will understand how the features of this invention provide its benefits. The benefits of this invention include, but are not limited to: low cost, ease of manufacture and use, storage of test results and an convenient way of comparing past test results with current test results electronically, and most important, testing with the eyelid closed to avoid irritating the patient's eye.

Without limiting the scope of this invention as expressed by the claims that follow, some, but not all, of its features are:

One, the tonometer device of this invention may include a probe having a bulbous-like end made of a flexible, resilient material adapted to contact the eye through the closed eyelid. The bulbous-like end has a hollow interior.

Two, a chamber within the probe may include the hollow interior of the bulbous-like end and a conduit extending from the hollow interior of the bulbous-like end along the probe. The chamber is at least partially filled with a fluid that moves within the chamber in response to the hollow interior of the bulbous-like end changing in volume as it bears against the eye. The fluid includes a liquid having two immiscible phases, one phase being non-conductive and the other phase being conductive.

Three, a first electrical connection may be at a first position along the conduit and a second electrical connection may be at a second position along the conduit. The conductive phase makes contact with the first electrical connection to complete a first electrical circuit when the conductive phase of the liquid reaches the first position and the intraocular pressure is at a first pressure. The conductive phase makes contact with the second electrical connection to complete a second electrical circuit when the conductive phase of the liquid reaches the second position and the intraocular pressure is at a second pressure. The second pressure typically is higher than the first pressure. A stop member may be employed to restrict the movement of the probe.

Four, a detector responsive to the movement of the fluid in the conduit may be used to provide a signal indicating the intraocular pressure. In one embodiment, the signal provides a visual indication that the intraocular pressure is at a safe level by turning on a light of one color or above the safe level by turning on a light of a different color.

In one embodiment, the probe may comprise a pair of arms pivotally connected at proximal ends of the arms. Each arm has a distal end adapted to make contact with the eye, and one of the distal ends has a pressure transducer thereat for detecting intraocular pressure. A stop member limits the distance the distal ends may be moved manually towards each other to apply essentially the same external pressure against the eye with each measurement of intraocular pressure. The detector responds to the transducer to provide a signal indicating the intraocular pressure. In one embodiment, the transducer comprises the bulbous-like member. An audio alarm may be activated when the arms are moved towards each other to a position at the end point of the test where distal ends are spaced apart a predetermined fixed distance which is the same for each measurement.

In one embodiment, a device for measuring and recording the intraocular pressure within an eye of a patient is provided. This device includes the probe having at a distal end a pressure transducer for detecting intraocular pressure. The pressure transducer provides an analog signal corresponding to the patient's intraocular pressure upon the probe contacting the eye of the patient. An analog to digital converter converts the analog signal into a digital signal corresponding to the patient's current measurement of intraocular pressure. A memory device stores information concerning the patient, including past measurements of the patient's intraocular pressure. This enables a comparison of past and present measurements to be made automatically with each measurement. A visual display device displays at least some of the information concerning the patient, including at least one past measurement of the patient's intraocular pressure and the current measurement of intraocular pressure. A microprocessor processes the digital signal corresponding to the patient's current measurement of intraocular pressure to the memory device and forwards a past and the current measurement of intraocular pressure to the display device.

This invention also includes a method of measuring intraocular pressure through the closed eyelid of a patient.

This method comprises the step of contacting the closed eyelid with a pressure transducer probe, typically one having a bulbous-like end as discussed above. The movement of the probe is limited. When the probe comprises a stop member and a pair of arms pivotally connected at one end, the arms are moved towards each other so that their distal ends are spaced apart a predetermined fixed distance upon engaging the stop member.

This invention also includes a method of detecting if the intraocular pressure within an eye is at a safe level. According to this method, an eye is contacted with an end of a probe to which is attached a resilient member with a hollow interior that decreases in volume as the member is pressed against the eye. The interior includes a liquid that moves in response to this change in volume. This movement is detected to determine if the intraocular pressure is at a safe level and then a signal is provided to indicate if at a safe or unsafe level exists.

DESCRIPTION OF DRAWINGS

Some embodiments of this invention, illustrating all its features, will now be discussed in detail. These embodiments depict the novel and non-obvious tonometer device and methods of this invention as shown in the accompanying drawings, which are for illustrative purposes only. These drawings include the following figures (FIGS.), with like numerals indicating like parts:

FIG. 1A is a schematic cross-sectional view of a non-compressible and non-conductive liquid being drawn into a primary conduit of the probe used in the tonometer depicted in FIG. 1.

FIG. 1B is a schematic cross-sectional view similar to that of FIG. 1A showing a non-compressible and conductive liquid being drawn into the primary conduit of the probe used in the tonometer depicted in FIG. 1.

FIG. 1C is a schematic cross-sectional view showing the primary conduit filled properly with fluid and sealed prior to being installed in the probe used in the tonometer depicted in FIG. 1.

FIG. 2A is a cross-sectional view taken along line 2A-2A of FIG. 1.

FIG. 2B is a plan view of the tonometer shown in FIG. 1 with sections broken away showing a coiled spring wound about a pivot pin connecting the proximal ends of the arms together.

FIG. 2C is an enlarged, fragmentary view showing the conductive liquid phase moved along the conduit to make contact with the second electrical connection.

DETAILED DESCRIPTION OF SOME EMBODIMENTS OF THIS INVENTION

A First Embodiment

Figure 1:
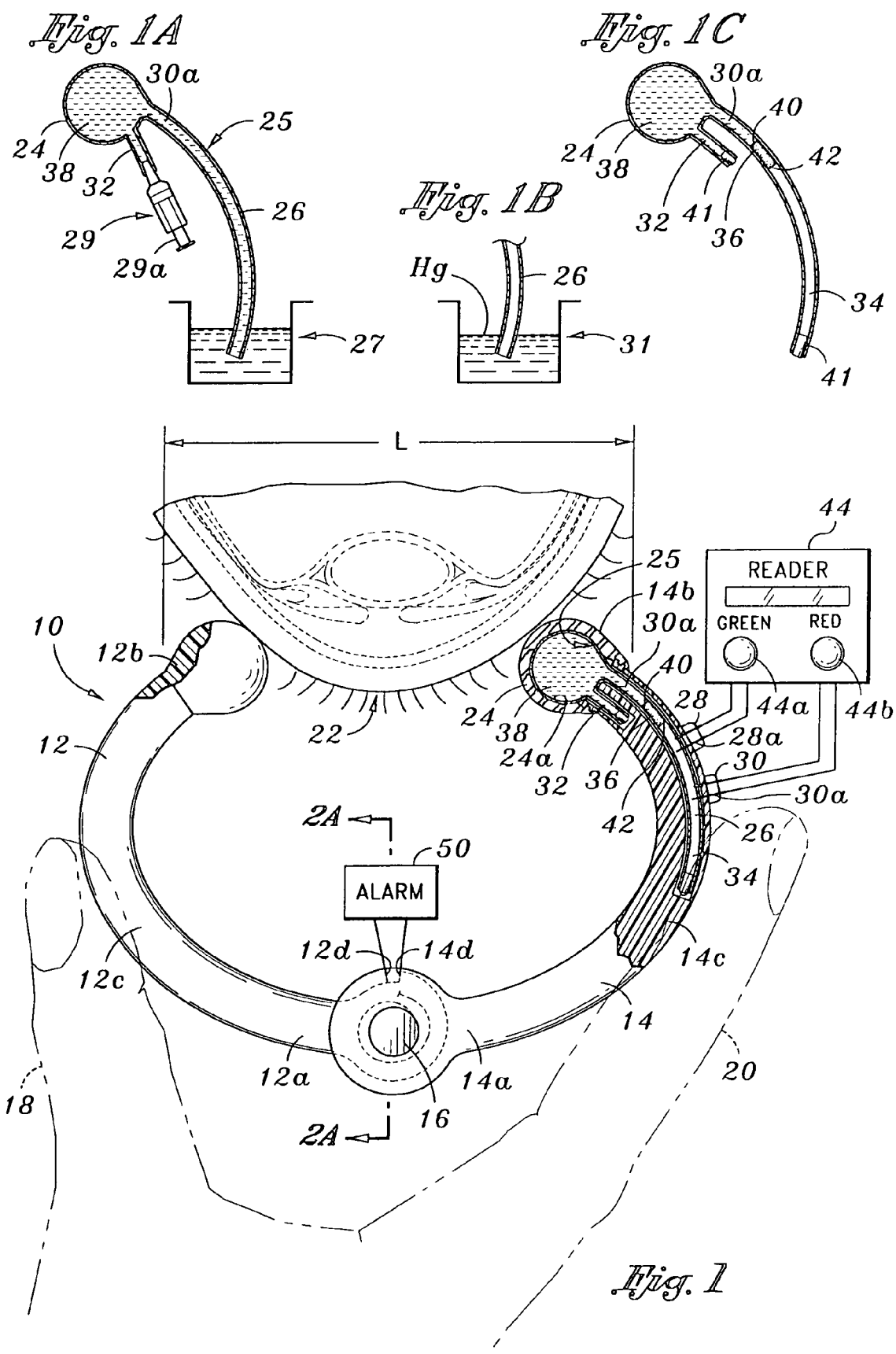
FIG. 1 is a schematic view of the tonometer of this invention with its arms spread apart and positioned against the closed eyelid of a patient.
Figure 2:
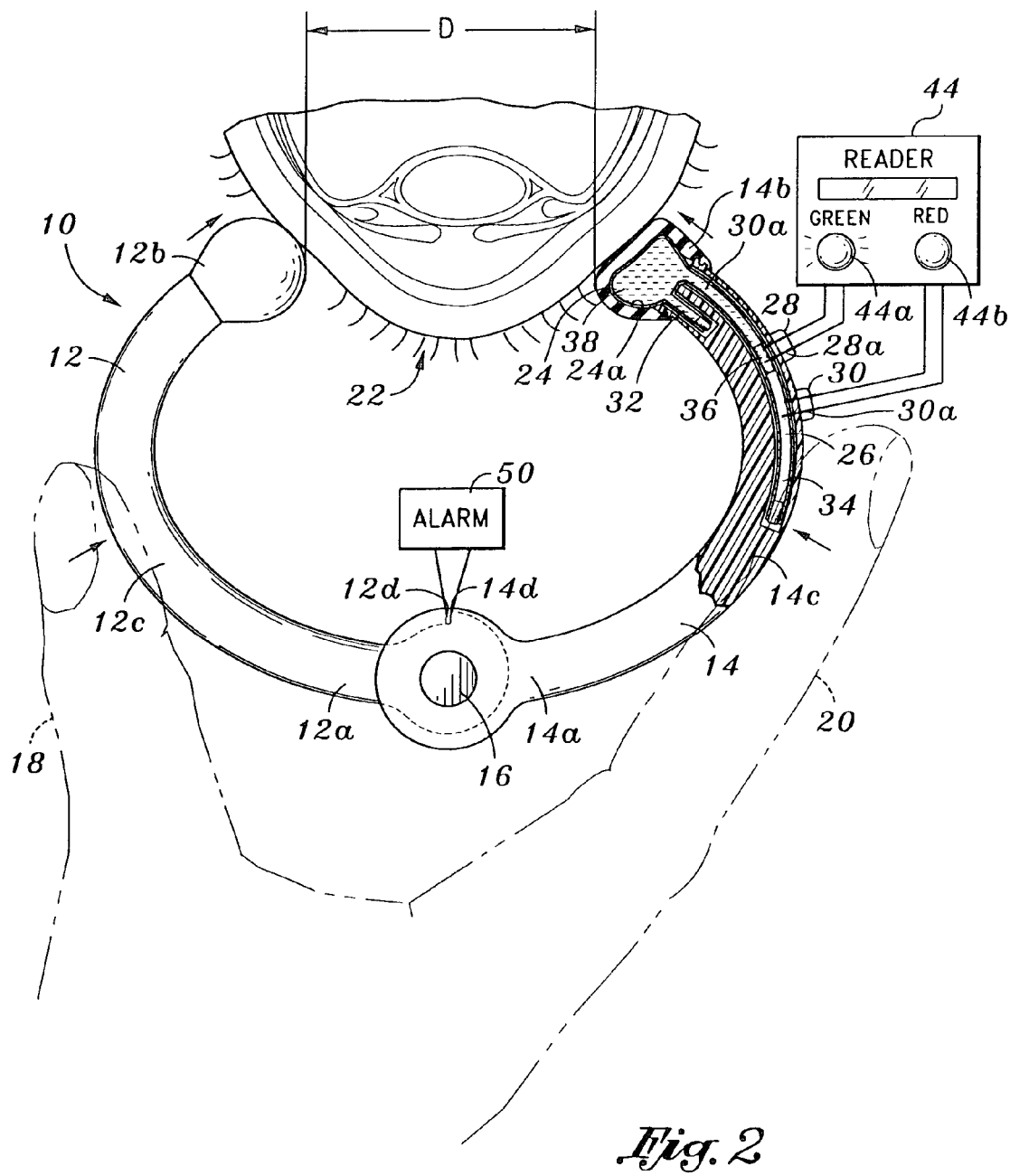
FIG. 2 is a schematic view similar to that shown in FIG. 1 showing the arms of the tonometer move towards each other.

As best illustrated in FIGS. 1-2C, the tonometer 10 of this invention comprises a pair of arms 12 and 14 having their respective proximal ends 12a and 14a mounted to a pivot pin 16. Using the thumb 18 and index finger 20, a user may manually move these arms 12 and 14 towards each other by simply applying pressure. This action moves the arms 12 and 14 from a first spaced apart position shown in FIG. 1 to a second spaced apart position shown in FIG. 2 where the respective distal ends 12b and 14b of these arms have been moved closer together. The distal ends 12b and 14b are initially placed, respectively, in the opposed extremities of a patient's closed eye. When the arms 12 and 14 are manually pushed together, pressure is applied to the eye through the patient's eyelid 22.

Each arm 12 and 14 has a curved section 12c and 14c respectively made of a plastic material, and there are shoulders 12d and 14d, respectively, at the proximal ends 12a and 14a of the arms 12 and 14. The distal end 12b of the arm 12 is substantially spherical. The distal end 14b of the other arm 14 has secured thereto a substantially spherical, hollow, flexible and resilient rubber bulb 24. This bulb 24 serves as a pressure transducer, and the one arm 14 constitutes a probe for detecting through the patient's closed eyelid 22 the intraocular pressure within the eye being tested.

As illustrated in FIG. 1A, an inner flexible skin 25 is used to create a chamber including the bulb 24 and a primary conduit 26 that extends along a substantial portion of the curved section 14c of the arm 14. Positioned at predetermined spaced apart locations along this primary conduit 26 are two pairs of electrical contacts 28 and 30, respectively. A secondary conduit 32 adjacent the primary conduit 26 is provided to enable the bulb 24 and primary conduit to be filled with fluid in a manner similar to that employed in making thermometers. Specifically, the flexible skin 25 has an open end of its one hallow leg corresponding to the primary conduit 26 is placed in a bowl 27 of distilled water and a syringe 29 is inserted into an open end of its other hallow leg corresponding to the secondary conduit 32. By pulling outward on the plunger 29a of the syringe 29, distilled water in drawn into the hallow interior of the bulb 24. Without completely draining the bulb 24, the open end of the hallow leg corresponding to the primary conduit 26 is placed in a bowl 31 containing a conductive liquid, for example, mercury (Hg). Again the syringe in pulled outward to draw mercury into the one hallow leg corresponding to the primary conduit 26. The open ends of the hallow legs corresponding to the conduits 26 and 32 are sealed off, for example, with plugs 41.

Consequently, there are three different fluid phases in the bulb 24 and primary conduit 26: (1) the gas phase 34 that is compressible and non-conductive, typically air; (2) the first liquid phase 36 that is essentially non-compressible and conductive, and (3) the second liquid phase 38 that is essentially non-compressible and non-conductive, typically distilled water. There is an interface 40 between the water phase 38 and mercury phase 36 and these two phases are immiscible with each other, and there is an interface 42 between the mercury phase 36 and the air phase 34 and these two phases are immiscible with each other. The mercury phase 36 is between the water phase 38 and the air phase 34. When the bulb 24 is compressed, water 38a from the bulb 24 pushes the mercury phase 36 along the primary conduit 26 towards the two pairs of electrical contacts 28 and 30.

As shown in FIG. 2C, when the mercury phase 36 contacts one or the other of the pairs of electrical contacts 28 and 30, an electrical circuit is completed in a visual display unit 44, including a green light 44a and a red light 44b. Each set of electrical contacts 28 and 30 is normally open, that is, there is a gap 28a and 30a between the pairs of electrical contacts. When the mercury phase 36 is moved next to the one pair of contacts 28, a circuit is completed including the mercury phase 36, the green light 44a, a battery (not shown) housed in the visual display unit 44, and the one pair of contacts 28. When the mercury phase 36 is moved next to the other pair of contacts 30, a circuit is completed including the mercury phase 36, the red light 44b, the battery, and the pair of contacts 30. Depending upon which circuit is completed, either the green light 44a or the red light 44b is illuminated during testing of the intraocular pressure of the patient's eye. The illumination of the green light indicates that the intraocular pressure of the patient's eye is normal, and the illumination of the red light indicates that the intraocular pressure of the patient's eye is excessively high.

As best illustrated in FIGS. 2, 2A, and 2B, a spring 48 is wound about the pivot pin 16. This spring 48 has a pair of free terminal ends A and B that are normally spaced apart when the arms 12 and 14 are spread apart as shown in FIG. 1. These free terminal ends A and B are position between the shoulders 12d and 14d at the proximal ends 12a and 14a of the arms 12 and 14. When the arms 12 and 14 are spread apart as shown in FIG. 1, the free terminal ends A and B of the spring 48 are separated. During testing, the arms 12 and 14 are moved towards each other until the shoulders 12d and 14d abut each other. Thus, the shoulders 12d and 14d act as stops preventing any further movement of the arms 12 and 14 towards each other. Consequently, there is a fixed predetermined distance between the distal ends 12b and 14b when the shoulders 12d and 14d abut each other.

When the shoulders 12d and 14d abut, the free terminal ends A and B are brought into contact with each other. As illustrated in FIG. 2, upon touching of the free terminal ends A and B, a circuit is completed for energizing an audio alarm 50. This circuit includes the alarm 50, a battery (not shown), and the spring 48, including its free terminal ends A and B that are now in contact. When the user releases his or her grasp of the arms 12 and 14, the spring 48 returns the arms to there normally spaced apart position illustrated in FIG. 1. Thus, during testing, the arms 12 and 14 are moved to bring the distal ends 12b and 14b towards each other so that they are always the same fixed predetermined distance at the "end point" of the test. In other words, the arms 12 and 14 are first spread apart a suitable distance so that the distal ends 12b and 14b make contact with the extremities of the closed eye through the eyelid 22 as shown in FIG. 1. Then the arms 12 and 14 are manually moved towards each until the shoulders 12d and 14d engage to moved the distal ends 12b and 14b into the same spaced apart relationship, the fixed distance D, regardless of the size of the eye of the patient being tested. This applies that same amount of pressure against the closed eyelid 22 for each different patient being tested.

In operation, as illustrated in FIGS. 1 and 2, the arms 12 and 14 are first separated a substantial distance from each other, but about equal to the length L of the patient's eye so that each distal end 12b and 14b will engage one extremity of the eye with the eyelid 22 closed. The distance D is shorter than the length L. The user, which may be the patient rather than a doctor, then manually pushes the arms 12 and 14 together using his or her thumb 18 and index finger 20, moving the distal ends 12b and 14b towards each other. As the bulb 24 is pressed against the closed eyelid 22, its shape changes, reducing the internal volume of its hollow interior 24a to push a portion of the water phase 38 in the bulb into the primary conduit 26. The amount the bulb 24 is deformed is proportional to the intraocular pressure within the eye being tested and the size and volume of the bulb 24 and primary conduit 26 are calibrated to detect when the intraocular pressure is normal or abnormally high. If the intraocular pressure is normal, the mercury phase 36 only moves to the position adjacent the first pair of contacts 28. In this case, an electric circuit is established including the mercury phase 36 causing the green light 44a on the display 44 to be illuminated. As best shown in FIG. 2C, if the intraocular pressure is abnormally high, the bulb 24 will be depressed even further, causing the mercury phase 36 to move along the primary conduit 26 to the position opposite the second pair of electrical contacts 30, completing a circuit to illuminate the red light 44b. Water 38a will be moved opposite the first pair of electrical contacts 28, but since the water is non-conductive, the green light 44a will not be lit.

When the arms 12 and 14 are moved to their maximum displacement towards each other, the fixed distance D, the shoulders 12d and 14d stop further movement and the free terminal ends A and B of the spring 48 make contact. This causes the audio alarm 50 to be energized and provide a sound signal that the end point of the test has been reached and the distal ends 12b and 14b of the arms 12 and 14 have been moved the proper distance D towards each other. The user may now observe the visual display 44 to see which light 44a or 44b is lit.

A Second Embodiment

Figure 3:
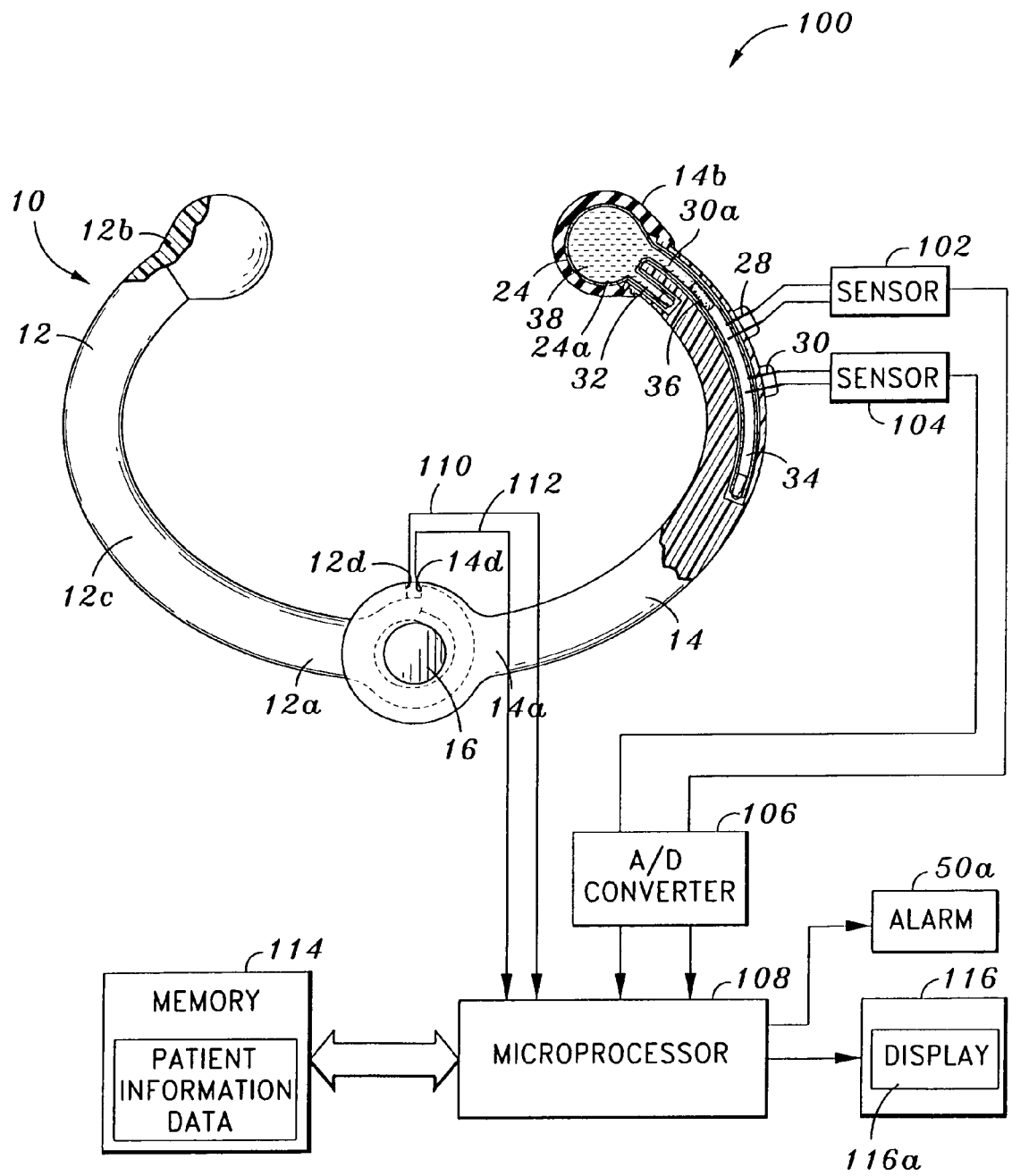
FIG. 3 is a schematic view of a second embodiment of the tonometer of this invention particularly adapted for use by physicians.

As illustrated in FIG. 3, a more elaborate tonometer 100 is provided for use by physicians. The arms 12 and 14 of this tonometer 100 are substantially the same as the arms in the tonometer 10 discussed above in connection with FIGS. 1 and 2, except the two pair of electrical contacts 28 and 30 along the primary conduit 26 are connected, respectively, through sensors 102 and 104 to the input of an analog to digital converter 106. The analog to digital converter 106 converts the analog signal detected as the mercury phase 36 moves past the one or the other sensor 102 or 104 to a digital signal. The analog to digital converter 106 has its outputs connected to a microprocessor 108. There are also electrical leads 110 and 112 from the shoulders 12d and 14d connected to the microprocessor 108. A memory device 114 is connected to the microprocessor 108 to enable two way transfer of information in the form of digital signals between the memory device and the microprocessor 108. The microprocessor 108 has one output connected to an audio alarm 50a and another output connected to a visual display unit 116 that has a screen 116a for displaying patient information that is collected during testing and past patient information, including previous test results, stored in the memory device 114.

When these arms 12 and 14 have been moved towards each other to the end point of the test when the shoulder 12d and 14d abut, the sensor 102 or 104 provide an analog signal corresponding to the intraocular pressure detected. The analog to digital converter 106 converts this analog signal into a digital signal that is forwarded by the microprocessor 108 to the memory device 114. At the same time the microprocessor 108 activates the audio alarm 50a and provides a numerical or alpha-numerical readout that is displayed on the screen 116a on the visual display unit 116. Thus, this tonometer 100 enables patient information and data to be collected and stored and compared with past test results, typically the last past measurement taken and stored in the memory device 114.

A Third Embodiment

Figure 4:
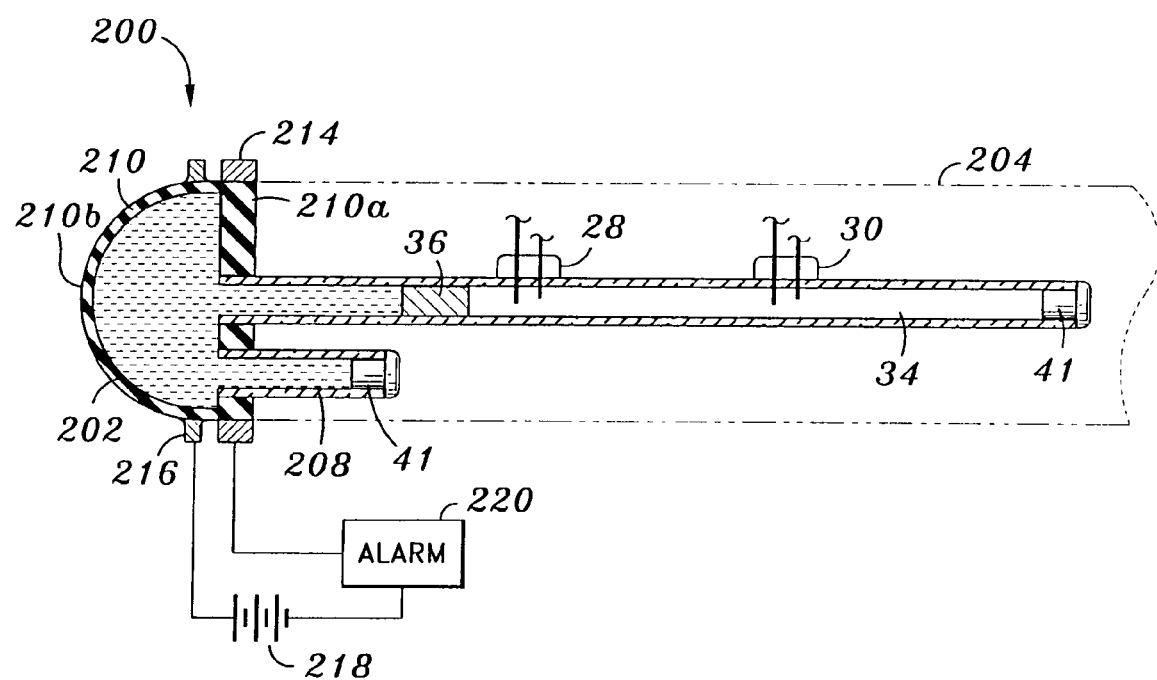
FIG. 4 is a schematic cross-sectional view of a third embodiment of the tonometer of this invention.

As illustrated in FIG. 4, a third embodiment of this invention, the tonometer 200, is provided employing a single probe 202. This probe 202 is encased with a housing 204 shown phantom lines and is connected to a visual display device that is essentially identical to the device 44 use in connection with first embodiment of this invention. The probe 202 includes a primary conduit 206 and secondary conduit 208, with the secondary conduit 208 having an open end with a plug 208a therein. Each conduit 206 and 208 is of tubular configuration and made of plastic. Air 34, a conductive liquid such as, for example, mercury 36, and a non-conductive liquid such as distilled water 38 are introduced into a hollow bulb 210 connected to the conduits 206 and 208 in the same manner as discussed above in construction the first embodiment. There are electrical contacts 28 and 30 along the longer conduit 206 which detect the mercury phase 36 moving along the long this conduit as the bulb 24 is compressed when it is pressed against the eye of the patient in a manner similar to that discussed above to turn on either the green light 44a or the red light 44b depending on the intraocular pressure within the patient's eye.

The base 210a of the bulb 210 is more rigid that its crown 210b which is flexible. A metal ring 214 is attached to the base 210a. There is a second metal ring 216 in coaxial alignment with, and spaced a predetermined distance X, from the metal ring 214. When the crown 210b is compressed during testing as the user pushes the crown against the closed eyelid 22, the ring 216 moves towards the ring 214. When these rings 214 and 216 abut, the end point of the test has been reached and a circuit including these rings, a battery 218 and audio alarm 220 is completed. This turns on the alarm 220. The user then looks at the visual display device 44 to see if the green light 44a or red light 44b has been illuminated, depending on the position of the mercury phase 36 in the conduit 206. When the tonometer 200 is moved away from the eye, the crown 210b has sufficient resiliency to act as a spring to return the bulb 210 to the position shown in FIG. 4 with the ring separated the distance X.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

The invention claimed is:

1. A device for measuring the intraocular pressure within an eye, including
    a pair of probe arms connected at proximal ends thereof to pivot, and
    one of said probe arms terminating in a distal end having a pressure transducer thereat that detects intraocular pressure,
    said pressure transducer including a flexible and resilient member having a hollow interior filled with a fluid.

2. A device of claim 1 including an audio alarm to indicate excessively high intraocular pressure.

3. A device of claim 1 including a visual display to indicate intraocular pressure.

4. A device for measuring the intraocular pressure within an eye, including
    a pair of probe arms connected at proximal ends thereof to pivot,
    a detector at a distal end of one of said probe arms that, upon said distal end contacting an eye, provides a signal indicating the intraocular pressure,
    said detector including a visual display comprising a first light of one color that indicates when lit that the intraocular pressure is normal and a second light of another color that indicates when lit that the intraocular pressure is excessively high.

5. A device for measuring the intraocular pressure within an eye, including
    a pair of probe arms connected at proximal ends thereof to pivot,
    a detector at a distal end of one of said probe arms that upon said distal end contacting an eye provides a signal indicating the intraocular pressure,
    said detector including a visual display that provides a numerical or alpha-numerical readout that is displayed on a screen of the visual display.

6. A device for measuring the intraocular pressure within an eye, including
    a pair of probe arms connected at proximal ends thereof to pivot, and
    one of said probe arms terminating in a distal end having a pressure transducer thereat that detects intraocular pressure, and
    a stop member that limits the distance the distal ends may be moved manually towards each other to apply essentially the same external pressure against the eye with each measurement of intraocular pressure.

7. A device of claim 6 including an audio alarm to indicate excessively high intraocular pressure.

8. A device of claim 6 including a visual display to indicate intraocular pressure.

9. A device for measuring the intraocular pressure within an eye, including
    a pair of probe arms connected at proximal ends thereof to pivot, and
    one of said probe arms terminating in a distal end having a pressure transducer thereat that detects intraocular pressure,
    said pressure transducer including a flexible and resilient member having a hollow interior filled with a fluid, and
    a stop member that limits the distance the distal ends may be moved manually towards each other to apply essentially the same external pressure against the eye with each measurement of intraocular pressure, and
    a visual display that indicates intraocular pressure.

10. A device of claim 9 where the visual display comprises a first light of one color that indicates when lit that the intraocular pressure is normal and a second light of another color that indicates when lit that the intraocular pressure is excessively high.

11. A device of claim 9 where the visual display provides a numerical or alpha-numerical readout that is displayed on a screen of the visual display.

* * * * *